United States Patent [19]

Pitzen et al.

[11] Patent Number: 4,813,870
[45] Date of Patent: Mar. 21, 1989

[54] DISPENSER FOR VISCOUS LIQUIDS

[75] Inventors: James F. Pitzen, St. Paul; Gerald E. Drake, Oakdale, both of Minn.

[73] Assignee: Minnesota Mining and Manufacturing Company, Saint Paul, Minn.

[21] Appl. No.: 23,665

[22] Filed: Mar. 9, 1987

[51] Int. Cl.$^4$ .............................................. A61C 5/04
[52] U.S. Cl. ..................................... 433/90; 604/224; 401/145; 401/172; 401/184; 222/207; 222/327; 222/390; 222/213
[58] Field of Search ................. 433/80, 81, 89, 90, 433/216; 222/213, 278, 327, 390, 495, 496, 209, 207, 210, 325, 326, 378; 604/207, 211, 224, 232; 401/172, 173, 174, 175, 145, 149, 184, 186

[56] References Cited

U.S. PATENT DOCUMENTS

| 1,724,617 | 8/1929 | Rapellin | 222/390 |
| 2,061,743 | 11/1936 | Tear | 74/424.8 |
| 2,745,575 | 5/1956 | Spencer | 222/327 |
| 2,772,817 | 12/1956 | Jauch | 222/207 |
| 3,002,517 | 10/1961 | Pitton | 222/327 |
| 3,462,840 | 8/1969 | Ellman | 32/60 |
| 3,902,815 | 9/1975 | Williams | 222/207 |
| 4,199,083 | 4/1980 | LoMaglio | 222/207 |
| 4,560,352 | 12/1985 | Neumeister et al. | 433/90 |
| 4,640,637 | 2/1987 | Winthrop | 401/145 |

FOREIGN PATENT DOCUMENTS 0105771 4/1984 European Pat. Off. .
3108179A1 3/1981 Fed. Rep. of Germany .
2341518 9/1977 France .

Primary Examiner—Samuel Scott
Assistant Examiner—Noah Kamen
Attorney, Agent, or Firm—Donald M. Sell; William L. Huebsch

[57] ABSTRACT

A dispenser for liquids including a cartridge containing a liquid, a nozzle, and a hollow flexible bladder between the cartridge and the nozzle. An assembly can be manually rotated to provide a high mechanical advantage and incrementally drive a piston through the cartridge to thereby fill the bladder with liquid from the cartridge and discharge any plug of solidified material (e.g., diluted phosphoric acid) that may be present in the nozzle; and manually operated button can be pressed to quickly and controllably collapse the bladder to thereafter dispel liquid within the bladder through the nozzle.

18 Claims, 3 Drawing Sheets

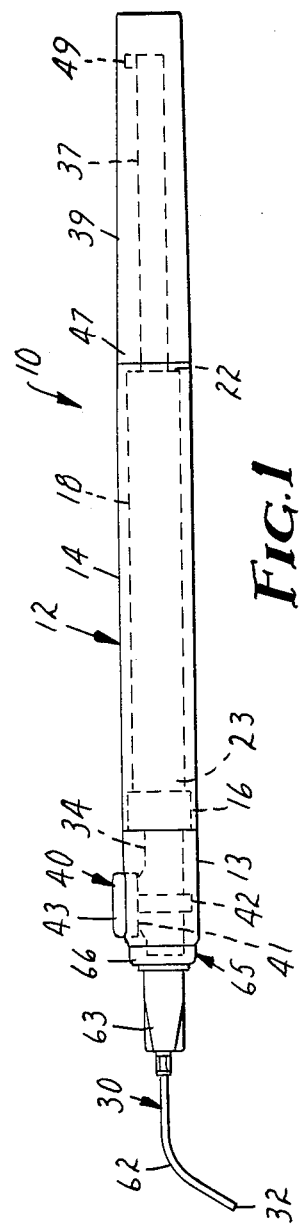
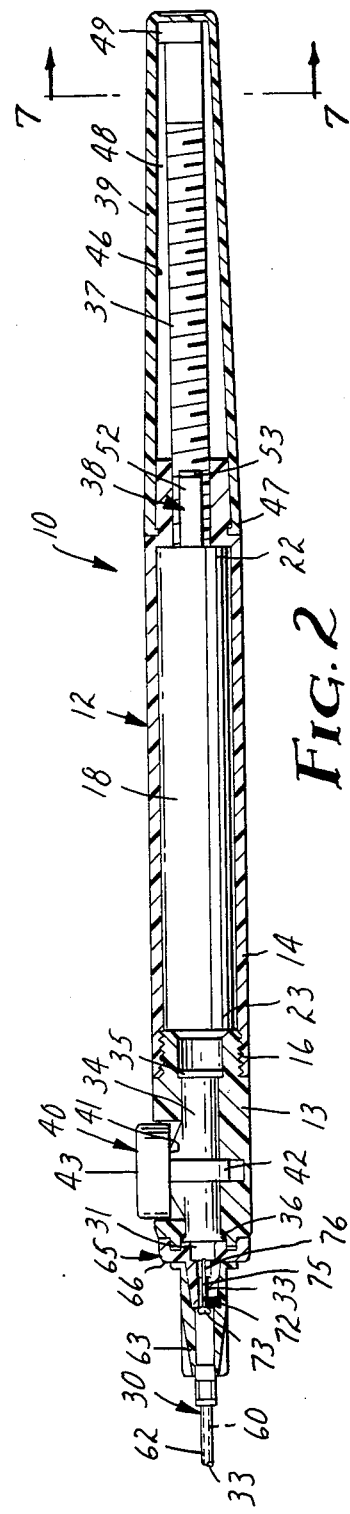

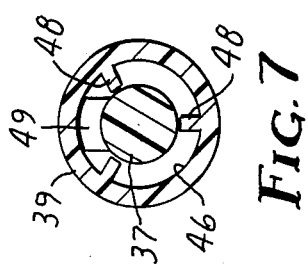 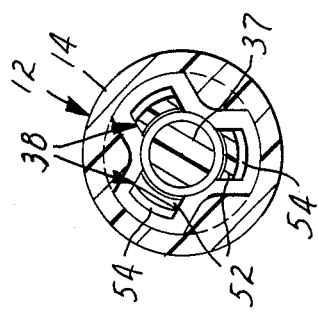
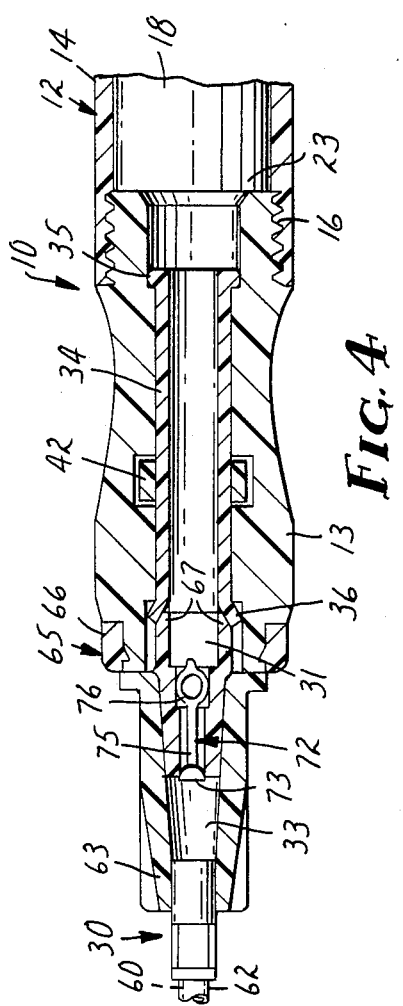 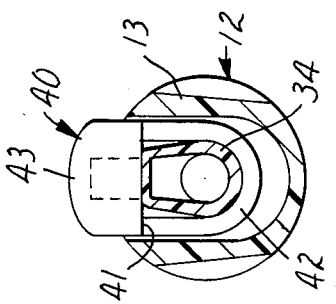

4,813,870

DISPENSER FOR VISCOUS LIQUIDS

TECHNICAL FIELD

The present invention relates to manually operated dispensers for dispensing controlled amounts of liquids, and in particular to such dispensers used by dentists to dispense viscous liquids into openings in teeth being restored.

BACKGROUND ART

Diluted phosphoric acid in the form of a viscous liquid is commonly used by dentists to help clean an opening in a tooth to be filled with a restorative material. Diluted phosphoric acid has commonly been dispensed through a conventional syringe. Any one application of the diluted phosphoric acid to a tooth requires only a small portion of the diluted phosphoric acid typically held by such a syringe, however, and between applications the diluted phosphoric acid has a tendency to solidify in the nozzle of the syringe due to exposure of the diluted phosphoric acid to the atmosphere thorough the outlet opening of the syringe. This solidified diluted phosphoric acid then forms a plug which must be expelled before the non-hardened diluted phosphoric acid can be expelled. Such expulsion of the plug of solidified diluted phosphoric acid is typically done by manually applying pressure against the plunger of the syringe, which pressure is hard to stop at the instant the plug is discharged s that a large unwanted amount of the liquid diluted phosphoric acid can also be discharged onto a patient's clothes or skin, or into the patient's mouth, which can result in damage or injury.

DISCLOSURE OF INVENTION

The present invention provides a manually operated dispenser for liquids including diluted phosphoric acid or other liquids such as dental sealing materials that allows the user to first, if necessary, easily clear any solidified material from a nozzle of the device without discharging substantially more than the solidified plug of material, and allows the user to quickly and controllably dispense or flow on the liquid as desired.

According to the present invention there is provided a dispenser for liquids comprising a housing including first and second generally tubular parts in axial alignment; a cartridge within the second housing part, the cartridge having an inner surface defining a through opening including a major portion of generally uniform cross section with rear and outlet ends, liquid within the through opening, and a piston in the through opening adjacent the rear end and adapted for sliding movement along the through opening in liquid tight sealing engagement with the inner surface. Also included is a nozzle having a small diameter through passageway fixed at the end of the first part of the housing opposite the second part; and a hollow flexible bladder mounted within and constrained against substantial radial expansion by the first part of the housing, which bladder has an inlet edge defining an inlet port communicating with the cartridge around the outlet opening, and an outlet edge defining an outlet port communicating with an inlet end of the nozzle around the passageway. Manually operated loading means are mounted on the second part of the housing at its end opposite the first part for providing a high mechanical advantage to incrementally drive the piston along the through opening from the rear toward the outlet end and to thereby fill the bladder and passageway of the nozzle with liquid from the cartridge and, if necessary, discharge any plug of solidified material that may be present in the passageway of the nozzle and for preventing movement of the piston away from the outlet end in response to pressure in the through passageway; and manually operated controlled dispensing means are mounted on the housing along the bladder for quickly and controllably compressing the bladder to dispel liquid within the bladder through the outlet port and the passageway in the nozzle.

Preferably the manually operated loading means comprises a threaded shaft centrally engaging the side of the piston opposite the bladder, a nut assembly mounted on the housing and threadably engaged with the threaded shaft, and manually actuated means for rotating the shaft in the nut assembly to drive the piston toward the outlet end of the through opening; and the nut assembly includes means for affording release of the engagement between the nut assembly and the threaded shaft to afford rapid movement of the threaded shaft through the nut assembly away from the nozzle assembly to facilitate loading a new cartridge assembly into the housing upon separation of the housing parts.

The manually operated means for quickly and controllably collapsing the bladder to dispel liquid within the bladder through the nozzle preferably comprises the first part of the housing having a side opening along the bladder, and a button projecting through the side opening, which button has an inner end in engagement with the bladder and an outer end adapted for manual engagement to press the button toward the bladder to compress it.

Also, preferably the housing and the manually actuatable means for rotating the shaft in the nut assembly are both elongate axially aligned members that provide a generally pen-like dispenser, and the nozzle is curved away from the side of the housing and can be oriented at different positions with respect to the button which facilitates easy use of the dispenser to dispense liquid into a patients mouth.

BRIEF DESCRIPTION OF THE DRAWING

The present invention will be further described with reference to the accompanying drawing wherein like parts are identified with like reference numerals in the several views, and wherein;

FIG. 1 is a side view of a dispenser according to the present invention;

FIG. 2 is an enlarged longitudinal sectional view of the dispenser shown in FIG. 1;

FIG. 4 is an enlarged fragmentary longitudinal sectional view of the dispenser shown in FIG. 1 taken along a plane disposed at ninety degrees to the view shown in FIG. 3;

FIG. 5 is a sectional view taken approximately along line 5—5 of FIG. 3; and

FIG. 6 is a sectional view taken approximately along line 6—6 of FIG. 3.

FIG. 7 is a sectional view taken approximately along line 7—7 of FIG. 3.

DETAILED DESCRIPTION

Figure 3:
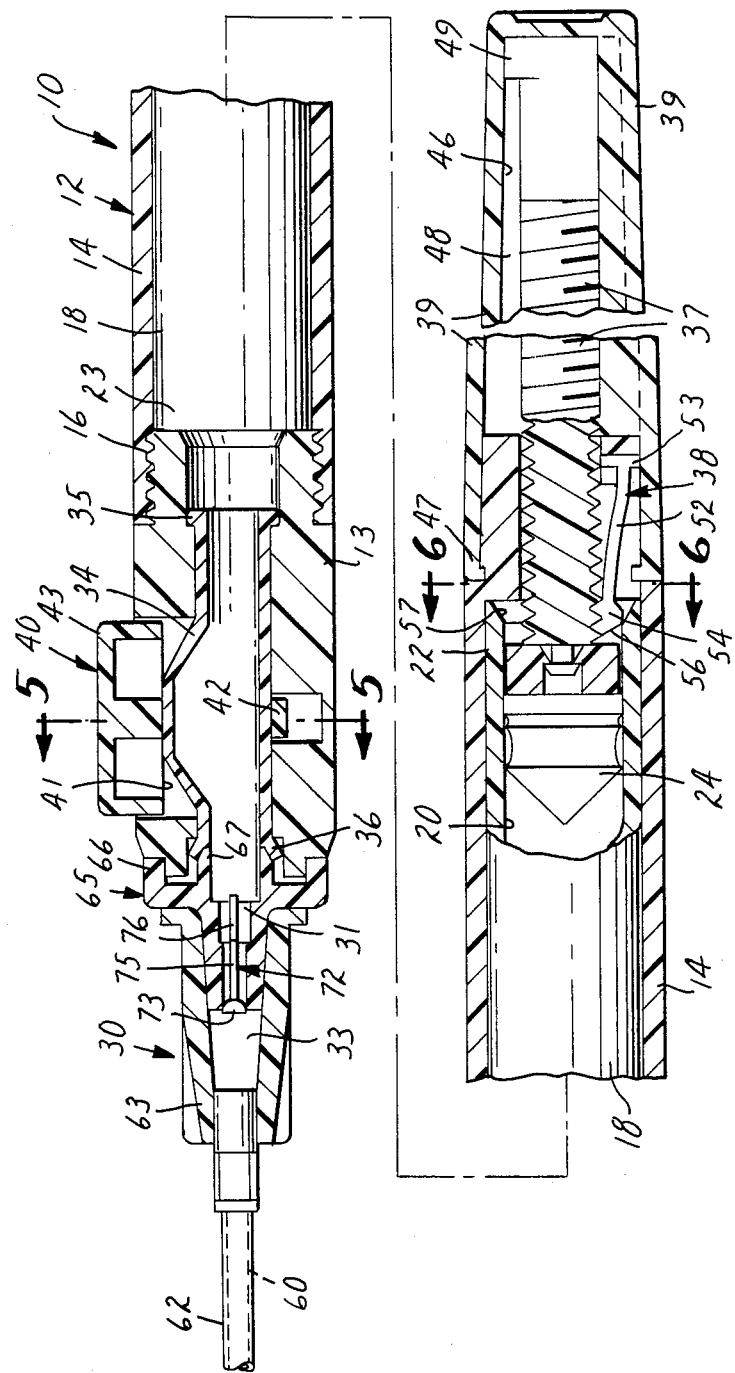
FIG. 3 is an enlarged fragmentary longitudinal sectional view of the dispenser shown in FIG. 1.

Referring now to the drawing, there is shown a dispenser for liquids according to the present invention, generally designated by the reference numeral 10.

The dispenser 10 comprises a housing 12 of polymeric material including first and second generally tubular parts 13 and 14 having central axes and releasably engaged with each other in axial alignment by threads 16 formed in their adjacent ends. A hollow cylindrical cartridge 18 is removably positioned in the second part 14 of the housing 12. The cartridge 18 has an inner surface 20 defining a through opening of generally uniform cross section with rear and outlet ends 22 and 23, which through opening is initially filled with the liquid to be dispensed when the cartridge 18 is placed in the dispenser 10 (which can be done by separating the housing 12 at the threads 16). The cartridge 18 includes a piston 24 in its through opening adjacent its rear end 22 and adapted for sliding movement along the through opening toward its outlet end 23 in liquid tight sealing engagement with the inner surface 20. Also included in the dispenser 10 is a nozzle 30 having an inlet end 31, an outlet end 32, and a through passageway 33 between the inlet and outlet ends 31 and 32 of substantially smaller cross sectional area than the through opening in the cartridge 18; and a hollow flexible bladder 34 mounted within and constrained against substantial radial expansion by the first part 13 of the housing 12, the bladder 34 having an inlet edge or flange 35 defining an inlet port and coupled to the cartridge 18 around the outlet end 23 of its through passageway because of compressive engagement between an end surface on a reduced diameter outlet part of the cartridge 18 with the flange 35 caused by threaded engagement of the housing parts 13 and 14, and an outlet edge or flange 36 defining an outlet port attached to the inlet end 31 of the nozzle 30 around the passageway 33.

Manually operated loading means are provided in the form of a threaded shaft 37 having an end adapted for engagement centrally with the side of the piston 24 opposite the outlet end 23 of the through opening in the cartridge 18, a nut assembly 38 mounted on the end of the second part 14 of the housing 12 opposite its first part 13 threadably engaged with the threaded shaft 37, and manually actuatable means including an elongate cup like shell 39 for rotating the threaded shaft 37 in the nut assembly 38 to drive the piston 24 toward the outlet end 23 of the through opening and thereby provide a high mechanical advantage for incrementally driving the piston 24 along the through opening from the rear end 22 toward the outlet end 23.

Also, manually operated controlled dispensing means are mounted on the housing 12 along the bladder 34 for quickly and controllably compressing the bladder 34 to dispel liquid within the bladder 34 through the outlet port and the passageway 33 in the nozzle 30, which means comprise the first part 13 of the housing 12 having a side opening along the bladder 34, and a button 40 projecting through the side opening. The button 40 has an inner end 41 in engagement with an outwardly bulging central portion of the bladder 34, an annular ring 42 around the bladder 34 that is received for sliding movement in a transverse slot in the first part 13 of the housing 12 to guide movement of the button 40 and is adapted to prevent movement of the button 40 outwardly through the side opening because of its engagement around the bladder 34, and an outer end 43 adapted for manual engagement to press the button 40 toward the bladder 34; the button 40 having sufficient height between its inner and outer ends to afford compressing the bladder 34 against the opposite inner wall of the housing 12.

As illustrated, the manually actuatable means for rotating the threaded shaft 37 in the nut assembly 38 comprises the elongate cup-like shell 39 which has an axis, an axially extending recess 46 opening through a first end 47 of the shell 39, and axially extending circumferentially spaced ribs 48 projecting radially inwardly into the recess 46 from the shell 39, a part of the shell 39 adjacent its first end 47 being journaled on the second part 14 of the housing 12 at its end opposite the first part 13 with the shaft 37 projecting into the recess 46 coaxially with the shell 39, and a lug 49 attached to the shaft 37 and projecting radially outwardly of the shaft 37 between the ribs 48 so that manual rotation of the shell 39 relative to the housing 12 will cause rotation of the shaft 37 by engagement of one of the ribs 48 with the lug 49, and the lug 49 can move along the ribs 48 as the shaft 37 moves axially relative to the housing 12.

The nut assembly 38 includes means for affording release of the engagement between the nut assembly 38 and the threaded shaft 37 to afford rapid movement of the threaded shaft 37 through the nut assembly 38 away from the nozzle 30 to facilitate loading a new cartridge 18 into the housing 12 upon separation of the housing parts 13 and 14. The nut assembly 38 comprises a plurality of or three finger like members 52 having first and second ends 53 and 54, the first ends 53 of the finger like members 52 being fixed to the second part 14 of the housing 12 in circumferentially spaced locations and the second ends 54 of the finger like members 52 projecting radially inwardly and toward the first part 13 of the housing 12. The second ends 54 of the finger like members 52 have threads formed thereon and the finger like members 52 are sufficiently flexible to afford movement of the second ends 54 of the finger like members 52 into and out of threaded engagement with the shaft 37. The second ends 54 of the finger like members 52 and the end of the cartridge 18 adjacent its rear end 22 have cam surfaces 56 and 57 respectively adapted for engagement to maintain the second ends 54 of the finger like members 52 in threaded engagement with the shaft 37 when the cartridge 18 is fully seated in the second part 14 of the housing 12. Thus the finger like members 52 and cam surfaces 56 and 57 provide means for affording release of the engagement between the nut assembly 38 and the threaded shaft 37 by separation of the cam surfaces 56 and 57 and flexing of the finger like members 52 away from the shaft 37 to afford rapid movement of the threaded shaft 37 through the nut assembly 38 away from the nozzle 30 to facilitate loading a new cartridge 18 into the housing upon separation of the housing parts 13 and 14.

As is best seen in FIGS. 1 through 4, the nozzle 30 is formed of several parts including a curved metal tube 60 curved away from the side of the housing 12 that provides the outlet end 32 of the nozzle 30, which tube 60 can be covered with a protective sleeve 62 of polymeric material that can be changed to facilitate sanitary use of the nozzle 30. The end of the tube 60 opposite its outlet end 32 is fixed in a collar 63 having a conical inner surface adapted for releasable frictional locking engagement with the conical outer surface of a support member 65 so that the tube 60 can be oriented at different positions with respect to the button 40 to facilitate dispensing the liquid to different places such as to an upper or lower surface in a patients mouth. The support member 65 has a central opening forming a part of the passageway 33, a flange 66 fixed as by a suitable adhesive to the first part 13 of the housing 12, and a tubular projection 67 that engages and makes sealing engagement with the outlet flange 36 on the bladder 34.

One way valve means are also provided in the nozzle 30 for allowing movement of the liquid from the bladder 34 through the passageway 33, while preventing movement of liquid in the passageway 33 back into the bladder 34. The one way valve means comprises a valve member 72 having at one end a hemispherical head 73 adapted to seal against a valve seat on an end surface of the flange 65 around the passageway 33 so that, when seated, the head 73 will prevent movement of liquid through the passageway 33 toward the bladder 34, a central stem 75 adapted to extend along the part of the passageway 33 in the flange 66, which stem 75 is of substantially smaller cross sectional area that the part of the passageway 33 through which it extends, and a biasing part 76 at its end opposite the head 73 that is annular around an axis transverse to the passageway 33 (FIG. 4) with a side of the biasing part 75 adjacent the head 73 supported against a ledge in the passageway 33 so that the head 73 is normally held against its seat. Pressure against the head 73 such as is caused by fluid flowing from the compressed bladder 34 will cause the head 73 to move away from its seat, thereby causing the normally annular biasing part 76 to resiliently elongate until the pressure is relieved, whereupon the biasing part 76 will recover its round shape and reposition the head 73 against its seat.

To use the dispenser 10 when the dispenser 10 is loaded with a cartridge 18 of liquid, a user first rotates the shell 39 relative to the housing 12 to move the piston 24 and thereby discharge liquid from the cartridge 18 into the bladder 34, after which the user can press the button 40 inwardly to compress the bladder 34 and thereby discharge fluid through the nozzle 30. If, prior to such a use, the liquid (e.g., diluted phosphoric acid) has solidified in the nozzle 30 due to exposure to the atmosphere, the high mechanical advantage applied through the shell 39, threaded shaft 37, and nut assembly 38 to move the piston 24 will afford easy discharge of the solidified plug from the nozzle 30 without also discharging a large amount of the liquid; whereas thereafter the liquid may be rapidly and controllably discharged by use of the button 40. When the cartridge 18 is emptied, it may easily be replaced by unscrewing the threads 16 joining the housing parts 13 and 14, and replacing the empty cartridge 18 in the second housing part 14 with a full one. Insertion of the full cartridge 18 into the second housing part 14 will push the threaded shaft 37 through the nut assembly 38, the threaded finger like members 52 of which are then not supported at their threaded distal ends 54 so that they will deflect away from the threaded shaft 37 to afford such movement. When the new cartridge 18 is fully inserted in the second part 14 of the housing 12, however, the generally conical cam surface 57 on the end of the cartridge 18 will engage the cam surfaces 56 on the threaded ends 54 of the finger like members 52 to engage, and thereafter hold the threads on those ends 54 in engagement with the threaded shaft 37 after the housing parts 13 and 14 are again attached by the threads 16.

The present invention has now been described with reference to one embodiment thereof. It will be apparent to those skilled in the art that many changes can be made in the embodiment described without departing from the scope of the present invention. Thus the scope of the present invention should not be limited to the structures descried in this application, but only by structures described by the language of the claims and the equivalents of those structures.

We claim:

1. A dispenser for liquids comprising:
   a housing including first and second coaxially aligned generally tubular parts releasably engaged with each other, said second part being adapted to receive a cartridge having an inner surface defining a through opening with the through opening comprising a major portion of generally uniform cross section and having rear and outlet ends, liquid within said through opening and a piston in said through opening adjacent said rear end adapted for sliding movement along said through opening in liquid tight sealing engagement with said inner surface;
   a nozzle having an inlet end fixed at the end of said first apart of said housing opposite said second part, an outlet end, and a through passageway between said inlet and outlet ends of substantially smaller cross sectional area than the through opening in the cartridge;
   a hollow flexible bladder mounted within and constrained against substantial radial expansion by the first part of said housing, said bladder having an inlet edge defining an inlet port adapted to communicate with said cartridge around said outlet opening, and an outlet edge defining an outlet port communicating with the inlet end of said nozzle around said passageway;
   loading means mounted on the second part of said housing at its end opposite said first part comprising a threaded shaft and a nut assembly threadably engaged with the threaded shaft, said shaft and said nut assembly being adapted for engagement between said housing and said piston to prevent movement of said piston along said through opening away from said outlet end in response to pressure in said through opening, and said loading means including means for affording manual rotation of said shaft and said nut assembly relative to each other to afford incremental driving of said piston along said through opening from said rear toward said outlet end with a high mechanical advantage to fill the bladder and passageway of the nozzle with liquid from the cartridge and discharge any plug of solidified material that may be present in the passageway of the nozzle; and
   manually operated controlled dispensing means mounted on said housing along said bladder for quickly and controllably compressing said bladder to dispel liquid within said bladder through the outlet port and the passageway in said nozzle.

2. A dispenser according to claim 1 wherein said threaded shaft has an end adapted for centrally engaging the side of said piston opposite said outlet end, said not assembly is mounted on the end of the second part of said housing opposite said first part, and said manually actuatable means rotates said shaft in said nut assembly to drive said piston toward the outlet end of said through opening.

3. A dispenser according to claim 2 wherein said nut assembly includes means for affording release of said engagement between said nut assembly and said threaded shaft to afford rapid movement of said threaded shaft through said nut assembly away from said nozzle to facilitate loading a new cartridge assembly into said housing upon separation of said housing parts.

4. A dispenser according to claim 2 wherein said manually actuatable means for rotating said shaft in said nut assembly comprises an elongate cup-like shell having an axis, an axially extending recess opening through a first end of said shell, and axially extending circumferentially spaced ribs projecting radially inwardly into said recess from said shell, a part of said shell adjacent said first end being journaled on said second part of the housing at its end opposite said first part with said shaft projecting into said recess coaxially with said shell, and a lug attached to said shaft and projecting radially outwardly of said shaft between said ribs so that manual rotation of said shell relative to said housing will cause rotation of said shaft by engagement of one of said ribs with said lug, and said lug can move along said ribs as said shaft moves axially relative to said housing.

5. A dispenser according to claim 2 wherein said nut assembly comprises a plurality of finger like members having first and second ends, said first ends of said finger like members being fixed to said second part of said housing in circumferentially spaced locations and said second ends of said finger like members projecting radially inwardly and toward said first part of said housing, the second ends of said finger like members having threads formed thereon and said finger like members being sufficiently flexible to afford movement of said second ends of said finger like members into and out of threaded engagement with said shaft, and wherein said second ends of said finger like members and said cartridge have cam surfaces adapted for engagement to maintain said second ends of said finger like members in threaded engagement with said shaft when said cartridge is in the second part of said housing, said finger like members and cam surfaces providing means for affording release of said engagement between said nut assembly and said threaded shaft by separation of said cam surfaces and flexing of said finger like members away from said shaft to afford rapid movement of said threaded shaft through said nut assembly away from said nozzle assembly to facilitate loading a new cartridge assembly into said housing upon separation of said housing parts.

6. A dispenser according to claim 1 wherein said housing and said manually operated means for driving said piston are both elongate axially aligned members that provide a generally pen-like dispenser, and said nozzle is curved away from one side of said housing.

7. A dispenser according to claim 1 wherein said manually operated means for quickly and controllably compressing said bladder to dispel liquid within said bladder through the outlet port and passageway in said nozzle comprises the first part of said housing having a side opening along said bladder, and a button projecting through said side opening, said button having an inner end in engagement with said bladder, and an outer end adapted for manual engagement to press said button toward said bladder, said button having sufficient height between said inner and outer ends to afford at least partially compressing said bladder in said housing.

8. A dispenser according to claim 7 wherein said manually operated means for incrementally driving said piston along said through opening comprises a threaded shaft adapted for centrally engaging the side of said piston opposite said bladder, a nut assembly mounted on the end of the second part of the housing opposite said first part and threadably engaged with said threaded shaft, and manually activated means for rotating said shaft in said nut assembly to drive said piston toward the outlet end of said through opening, said housing and said means adapted for manual rotation both being elongate axially aligned members that provide a generally pen-like dispenser, and said nozzle being curved away from the side of said housing.

9. A dispenser according to claim 1 further including one way valve means for allowing movement of the liquid from the bladder through the passageway in the nozzle while preventing movement of the liquid in the passageway back into the bladder.

10. A dispenser for liquids comprising:
a housing including first and second generally tubular parts in axial alignment;
a cartridge within said second part, said cartridge having an inner surface defining a through opening with the through opening comprising a major portion of generally uniform cross section and having rear and outlet ends, a liquid within said through opening, and a piston in said through opening adjacent said rear end and adapted for sliding movement along said through opening in liquid tight sealing engagement with said inner surface;
a nozzle having an inlet end fixed at the end of said first part of said housing opposite said second part, an outlet end, and a through passageway between said inlet and outlet ends of substantially smaller cross sectional area than the through opening in said cartridge;
a hollow flexible bladder mounted within and constrained against substantial radial expansion by the first part of said housing, said bladder having an inlet edge defining an inlet port communicating with said cartridge around said outlet opening, and an outlet edge defining an outlet port communicating with the inlet end of said nozzle around said passageway;
loading means mounted on the second part of said housing at its end opposite said first part comprising a threaded shaft and a nut assembly threadably engaged with the threaded shaft, said shaft and said nut assembly being adapted for engagement between said housing and said piston to prevent movement of said piston along said through opening away from said outlet end in response to pressure in said through opening, and said loading means including means for affording manual rotation of said shaft and said nut assembly relative to each other to afford incremental driving of said piston along said through opening from said rear toward said outlet end with a high mechanical advantage to fill the bladder and passageway of the nozzle with liquid from the cartridge and discharge any plug of solidified material that may be present in the passageway of the nozzle; and
manually operated controlled dispensing means mounted on said housing along said bladder for quickly and controllably compressing said bladder to dispel liquid within said bladder through the outlet port and the passageway in said nozzle.

11. A dispenser according to claim 10 wherein said threaded shaft has an end centrally engaging the side of said piston opposite said bladder, said nut assembly is mounted on the end of the second part of said housing opposite said first part, and said manually actuatable means rotates said shaft in said nut assembly to drive said piston toward the outlet end of said through opening.

12. A dispenser according to claim 11 wherein said nut assembly includes means for affording release of said engagement between said nut assembly and said threaded shaft to afford rapid movement of said threaded shaft through said nut assembly away from said nozzle assembly to facilitate loading a new cartridge assembly into said housing upon separation of said housing parts.

13. A dispenser according to claim 11 wherein said housing and said manually activated means for rotating said shaft are both elongate axially aligned members that provide a generally pen-like dispenser, and said nozzle is curved away from the side of said housing.

14. A dispenser according to claim 11 wherein said manually actuatable means for rotating said shaft in said nut assembly comprises an elongate cup-like shell having an axis, an axially extending recess opening through a first end of said shell, and axially extending circumferentially spaced ribs projecting radially inwardly into said recess from said shell, a part of said shell adjacent said first end being journaled on said second part of the housing at its end opposite said first part with said shaft projecting into said recess coaxially with said shell, and a lug attached to said shaft and projecting radially outwardly of said shaft between said ribs so that manual rotation of said shell relative to said housing will cause rotation of said shaft by engagement of one of said ribs with said lug, and said lug can move along said ribs as said shaft moves axially relative to said housing.

15. A dispenser according to claim 11 wherein said nut assembly comprises a plurality of finger like members having first and second ends, said first ends of said finger like members being fixed to said second part of said housing in circumferentially spaced locations and said second ends of said finger like members projecting radially inwardly and toward said first part of said housing, the second ends of said finger like members having threads formed thereon and said finger like members being sufficiently flexible to afford movement of said second ends of said finger like members into and out of threaded engagement with said shaft, and wherein said second ends of said finger like members and said cartridge have cam surfaces adapted for engagement to maintain said second ends of said finger like members in threaded engagement with said shaft when said cartridge is in the second part of said housing, said finger like members and cam surfaces providing means for affording release of said engagement between said nut assembly and said threaded shaft by separation of said cam surfaces and flexing of said finger like members away from said shaft to afford rapid movement of said threaded shaft through said nut assembly away from said nozzle assembly to facilitate loading a new cartridge assembly into said housing upon separation of said housing parts.

16. A dispenser according to claim 10 wherein said manually operated means for quickly and controllably compressing said bladder to dispel liquid within said bladder through the outlet port and passageway in said nozzle comprises the first part of said housing having a side opening along said bladder, and a button projecting through said side opening, said button having an inner end in engagement with said bladder, and an outer end adapted for manual engagement to press said button toward said bladder, said button having sufficient height between said inner and outer ends to afford compressing said bladder in said housing.

17. A dispenser according to claim 16 wherein said manually operated means for incrementally driving said piston along said through opening comprises a threaded shaft centrally engaging the side of said piston opposite said bladder, a nut assembly mounted on the end of the second part of said housing opposite said first part and threadably engaged with said threaded shaft, and manually actuatable means for rotating said shaft in said nut assembly to drive said piston toward the outlet end of said through opening, said housing and said manually actuatable means for rotating said shaft both being elongate axially aligned members that provide a generally pen-like dispenser, and said nozzle being curved away from the side of said housing.

18. A dispenser according to claim 10 further including one way valve means for allowing movement of the liquid from the bladder through the passageway in the nozzle while preventing movement of the liquid in the passageway back into the bladder.

* * * * *